United States Patent
Fischell et al.

(10) Patent No.: US 6,706,061 B1
(45) Date of Patent: Mar. 16, 2004

(54) ENHANCED HYBRID CELL STENT

(76) Inventors: Robert E. Fischell, 14600 Viburnum Dr., Dayton, MD (US) 21036; David R. Fischell, 71 Riverlawn Dr., Fair Haven, NJ (US) 07704; Tim A. Fischell, 6447 Whitney Woods, Richland, MI (US) 49083

( * ) Notice: Subject to any disclaimer, the term of this patent is extended or adjusted under 35 U.S.C. 154(b) by 290 days.

(21) Appl. No.: 09/718,558

(22) Filed: Nov. 22, 2000

Related U.S. Application Data

(63) Continuation-in-part of application No. 09/607,980, filed on Jun. 30, 2000, now abandoned.

(51) Int. Cl.$^7$ .................................................. A61F 2/06
(52) U.S. Cl. ..................................................... 623/1.15
(58) Field of Search .............................. 623/1.15–1.21, 623/1.35, 1.36, 1.25

(56) References Cited

U.S. PATENT DOCUMENTS

| | | | |
|---|---|---|---|
| 3,657,744 A | 4/1972 | Ersek | |
| 4,441,216 A | 4/1984 | Ionescu et al. | |
| 4,503,569 A | 3/1985 | Dotter | |
| 4,553,545 A | 11/1985 | Maass et al. | |
| 4,580,568 A | 4/1986 | Gianturco | |
| 4,733,665 A | 3/1988 | Palmaz | |
| 4,776,337 A | 10/1988 | Palmaz | |
| 4,800,882 A | 1/1989 | Gianturco | |
| 4,856,516 A | 8/1989 | Hillstead | |
| 4,886,062 A | 12/1989 | Wiktor | |
| 4,907,336 A | 3/1990 | Gianturco | |
| 4,969,458 A | 11/1990 | Wiktor | |
| 4,990,131 A | 2/1991 | Dardik et al. | |

(List continued on next page.)

FOREIGN PATENT DOCUMENTS

| | | |
|---|---|---|
| DE | 32 05 942 A1 | 9/1983 |
| EP | 0 540 290 A3 | 5/1993 |
| EP | 0 540 290 A2 | 5/1993 |
| EP | 0 800 801 A1 | 10/1997 |
| EP | 0 824 900 A2 | 2/1998 |
| EP | 0 830 853 A1 | 3/1998 |
| EP | 0 734 698 B1 | 8/1998 |
| EP | 0 916 317 A1 | 5/1999 |
| FR | 566 8074 | 2/1924 |
| GB | 0 662 307 A2 | 12/1951 |
| GB | 1 205 743 A5 R | 9/1970 |
| WO | WO 96/26689 A1 | 9/1996 |
| WO | WO 96/34580 A1 | 11/1996 |
| WO | WO 97/25000 A1 | 7/1997 |
| WO | WO 98/19628 A1 | 5/1998 |

Primary Examiner—Michael J. Milano
Assistant Examiner—(Jackie) Tan-Uyen T. Ho

(57) ABSTRACT

Disclosed is an open cell stent that has adjacent sets of circumferential struts connected by means of highly flexible, undulating, connecting struts. To decrease outward flaring of the circumferential struts when the pre-deployed stent is advance through highly curved vessels, each unconnected strut of the sets of circumferential struts has a decreased longitudinal length as compared to the longitudinal length of the circumferential struts that are connected by the flexible connecting struts. To decrease the propensity for outward flaring of the end set of circumferential struts, the longitudinal length of the end set of circumferential struts is shorter than the longitudinal length of the interior set of circumferential struts. Enhanced features of the circumferential sets of strut members of the stent are also disclosed. Specifically, variable strut width for the curved sections and the diagonal sections of the circumferential sets of strut members can be employed to enhance the stents radial rigidity and to provide enhanced radiopacity of the end sets of strut members compared to the radiopacity of the interior sets of strut members.

20 Claims, 7 Drawing Sheets

U.S. PATENT DOCUMENTS

| | | |
|---|---|---|
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco et al. |
| 5,041,126 A | 8/1991 | Gianturco |
| 5,064,435 A | 11/1991 | Porter |
| 5,102,417 A | 4/1992 | Palmaz |
| 5,104,404 A | 4/1992 | Wolff |
| 5,116,365 A | 5/1992 | Hillstead |
| 5,122,154 A | 6/1992 | Rhodes |
| 5,131,908 A | 7/1992 | Dardik et al. |
| 5,133,732 A | 7/1992 | Wiktor |
| 5,135,536 A | 8/1992 | Hillstead |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,307 A | 3/1993 | Wall |
| 5,195,984 A | 3/1993 | Schatz |
| 5,217,483 A | 6/1993 | Tower |
| 5,222,971 A | 6/1993 | Willard et al. |
| 5,246,445 A | 9/1993 | Yachia et al. |
| 5,258,021 A | 11/1993 | Duran |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,334,301 A | 8/1994 | Heinke et al. |
| 5,342,387 A | 8/1994 | Summers |
| 5,354,257 A | 10/1994 | Roubin et al. |
| 5,354,308 A | 10/1994 | Simon et al. |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,382,261 A | 1/1995 | Palmaz |
| 5,387,235 A | 2/1995 | Chuter |
| 5,389,106 A | 2/1995 | Tower |
| 5,395,390 A | 3/1995 | Simon et al. |
| 5,397,355 A | 3/1995 | Marin et al. |
| 5,403,341 A | 4/1995 | Solar |
| 5,405,377 A | 4/1995 | Cragg |
| 5,411,549 A | 5/1995 | Peters |
| D359,802 S | 6/1995 | Fontaine |
| 5,421,955 A | 6/1995 | Lau et al. |
| 5,423,885 A | 6/1995 | Williams |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,474,563 A | 12/1995 | Myler et al. ................ 606/108 |
| 5,496,365 A | 3/1996 | Sgro |
| 5,527,354 A | 6/1996 | Fontaine et al. |
| 5,569,295 A | 10/1996 | Lam |
| 5,591,197 A | 1/1997 | Orth et al. |
| 5,632,763 A | 5/1997 | Glastra |
| 5,643,312 A | 7/1997 | Fischell et al. |
| 5,649,952 A | 7/1997 | Lam |
| 5,653,747 A | 8/1997 | Dereume |
| 5,669,924 A | 9/1997 | Shaknovich |
| 5,697,971 A | 12/1997 | Fischell et al. |
| 5,725,572 A * | 3/1998 | Lam et al. ................ 623/1.16 |
| 5,755,734 A | 5/1998 | Richter et al. |
| 5,792,144 A * | 8/1998 | Fischell et al. ............. 606/108 |
| 5,800,508 A | 9/1998 | Goicoechea et al. |
| 5,824,049 A | 10/1998 | Ragheb et al. |
| 5,861,027 A | 1/1999 | Trapp |
| 5,876,449 A | 3/1999 | Starck et al. |
| 5,911,754 A | 6/1999 | Kanesaka et al. |
| 5,913,895 A * | 6/1999 | Burpee et al. ............... 623/1.2 |
| 6,190,403 B1 | 2/2001 | Fischell et al. |
| 6,190,406 B1 * | 2/2001 | Duerig et al. ................ 623/1.2 |
| 6,224,626 B1 * | 5/2001 | Steinke ...................... 623/1.16 |
| 6,264,688 B1 | 7/2001 | Herklotz et al. ........... 623/1.16 |

\* cited by examiner

FIG. 2 "PRIOR ART"

ENHANCED HYBRID CELL STENT

This is a continuation-in-part application of Ser. No. 09/607,980, filed by the same co-inventors on Jun. 30, 2000, now abandoned.

FIELD OF USE

This invention is in the field of stents for implantation into a vessel of a human body.

BACKGROUND OF THE INVENTION

Stents are well known medical devices that have been used for maintaining the patency of a large variety of vessels of the human body. The most frequent use is for implantation into the coronary vasculature. Although stents have been used for this purpose for more than ten years, many stent designs still lack the required flexibility and radial rigidity to provide an optimum clinical result. Another deficiency of open cell stents is that some stent struts members can flare outward (fish scaling) as the stent is advanced through a tight curve.

An open cell stent is defined as a stent that has circumferential sets of strut members with some curved sections (crowns) that are not connected by a longitudinal connecting link to an adjacent circumferential set of strut members. In comparison, a closed cell stent has every curved section of every circumferential set of strut members, except at the distal and proximal ends of the stent, attached to a longitudinal connecting link. A strut member whose curved section is not attached to a longitudinal connecting link is defined as an unconnected strut member.

There are several "open cell" stents that are currently being marketed for the treatment of coronary stenoses. Examples of these are the Tetra stent from Guidant Corporation and the S670 stent from Medtronics, Inc. Each of these stents has a limited number of straight longitudinal connecting links to join adjacent curved sections of adjacent circumferential sets of strut members. These straight longitudinal connecting links can cause outward flaring of the end circumferential sets of strut members as the stent bends around a curve. The interior unconnected strut members also can flare outward when the pre-deployed stent mounted on a balloon is advanced through a curved vessel such as a coronary artery. Any strut that flares outward can engage the vessel wall during stent delivery in a curved vessel thereby preventing the stent from reaching the site that is to be stented.

Most current open cell stents use a multiplicity of circumferential sets of strut members connected by straight longitudinal connecting links. The circumferential sets of strut members are typically formed from a series of diagonal sections connected to curved sections forming a closed-ring, zig-zag structure. This structure opens up as the stent expands to form the element in the stent that provides structural support for the arterial wall. A single strut member is defined as a diagonal section connected to a curved section within one of the circumferential sets of strut members. In current open cell stent designs such as the Tristar stent (Guidant Corp.) these sets of strut members are formed from a single piece of metal having a uniform wall thickness and uniform strut width. Although a stent with uniform width of the strut members will function, if the width is increased to add strength or radiopacity, the sets of strut members will experience increased strain upon expansion. High strain can cause cracking of the metal and potential fatigue failure of the stent under the cyclic stress of a beating heart.

Existing highly radiopaque stents such as the Crossflex coil stent (made from 0.005 inch diameter tantalum wire) by Cordis Corp. and the gold plated NIROYAL stent made by the Boston Scientific Co. can obscure the inside of the vessel because of the high radiopacity over the entire length of the stent. The Be stent of Medtronics, Inc., has small gold markers at the ends of the stent but those markers only mark an end point without allowing visualization of the entire end set of strut members. Fischell et al in U.S. Pat. No. 6,086,604 teaches a closed cell stent with the end sets of strut members being gold plated. Such a stent would have ideal radiopacity but could (like the Be stent) exhibit corrosion due to dissimilar metals placed in an electrolytic solution such as the blood. There has also been significant evidence that gold is a poor surface material for stents because it can increase the risk of subacute thrombosis and restenosis.

Fischell et al in U.S. Pat. No. 5,697,971 show in FIG. 7 a stainless steel stent with increased width diagonal sections in all the circumferential sets of strut members. The U.S. Pat. No. 5,697,971 does not teach the use of a variable width for diagonal sections as a means to tailor the stent radiopacity. The U.S. Pat. No. 5,697,971 also does not teach specific metals and alloys having greater radiopacity than stainless steel, nor does it teach the use of the alternating curved sections and diagonal sections to form the circumferential sets of strut members. Furthermore, the U.S. Pat. No. 5,697,971 does not teach the use of variable width of curved sections that can provide additional radial rigidity and/or variable width diagonal sections to create relatively greater radiopacity for the end set of strut members.

SUMMARY OF THE INVENTION

The present invention is an open cell stent that is designed to optimize many of the operating parameters that are expected for stents in the first decade of the 21st century. Specifically, an optimum stent design would have the following characteristics:

I. IN THE PRE-DEPLOYED STATE
  1. excellent flexibility
  2. low profile (i.e.; small outside diameter of the stent)
  3. good radiopacity
  4. smooth outer surface
  5. no flaring of struts when advancing through curved arteries
  6. a high degree of stent retention onto the delivery catheter II. AFTER DEPLOYMENT
  1. flexible so as to conform to a curved artery
  2. radially rigid (i.e.; low recoil)
  3. good radiopacity
  4. good coverage of the vessel wall (i.e.; no plaque prolapse)
  5. side branch access without strut breakage
  6. minimal foreshortening compared to the length of the stent in its pre-deployed state Although many desirable attributes are required of the catheter that is used to deliver the stent, the scope of the present invention is limited to the design of the stent itself However, it should be understood that the reduced foreshortening of this stent is a result of having undulating longitudinal connecting links that readily extend in their longitudinal length when the balloon onto which the stent is crimped is inflated.

To accomplish the goals listed in I. and II. above, the stent would optimally have at least two open cells around the circumference of the stent. A unique feature of the present invention is that each of the strut members whose curved sections are unconnected has a shorter longitudinal length as compared to the longitudinal length of the strut members that are connected by a longitudinal connecting link. This shorter length (optimally on the order of at least 0.1 mm shorter) reduces outward flaring of the unconnected strut members when the stent is advanced through highly curved vessels such as some coronary arteries. Flaring (which is sometimes called "fish-scaling") can cause the stent to engage the vessel wall as the stent is advanced through curved arteries thus precluding delivery of the stent to its intended location.

Another novel feature of this stent is that the longitudinal connecting links can have an undulating shape so that they can easily expand or contract in their longitudinal length when the stent is advanced through a curved vessel. The extraordinary capability of this stent to bend easily is a combination of the fact that those curved sections of adjacent circumferential sets of strut members that are connected are connected with flexible longitudinal connecting links, and many (typically one-half) of the curved sections are unconnected. Of course, the weakest possible connection that provides the highest degree of longitudinal flexibility is being unconnected. Therefore, the combination of no connections plus the few required connections between the circumferential sets of strut members being by means of highly flexible undulating longitudinal connecting links imparts to this stent an extraordinarily high degree of longitudinal flexibility.

It should also be understood that all the strut members at each end of the stent should also have a shortened longitudinal length because the outside curved section of the end circumferential sets of strut members cannot be connected to any adjacent circumferential set of strut members. By shortening all the end strut members, end flaring of the stent as it is advanced through curved vessels can be reduced. Furthermore, the fact that the interior curved sections of each strut member at the ends of the stent either have no connection or a flexible, undulating longitudinal connecting link connection to an inner strut members is desirable in preventing flaring out of the strut members at the ends of the stent. This is not the case for strut members that have a straight connection to an end circumferential strut such as shown in FIG. 5 of U.S. Pat. No. 5,759,192.

Good radiopacity for the stent is achieved by having a stainless steel stent that has a wall thickness that is the least 0.0045 inches. Another means would be to use a metal with a higher density such as tantalum with a thickness greater than 0.002 inches. A third means for obtaining improved radiopacity would be to sandwich a high density metal between two layers of stainless steel with each of the co-axial tubes having a wall thickness between 0.001 and 0.002 inches.

Another feature of the present invention is that the undulating longitudinal connecting links readily extend in the longitudinal direction when the balloon is inflated. Since the circumferential sets of strut members upon deployment tend to decrease in their longitudinal length, the longitudinal lengthening of the undulating longitudinal connecting links has the effect of minimizing the foreshortening of the deployed stent.

To optimize radiopacity, the ideal radiopaque, open cell stent would have end sets of strut members that are highly radiopaque so that they can be readily seen even using low power fluoroscopy with an interior section of the stent that is visible but not too bright so as to obscure the lumen when high power cine film angiograms are taken. The stent should also have only one material on its outside surface to avoid potential corrosion and that material should not promote subacute thrombosis or restenosis.

The present invention is an open cell stent stent that is designed to have optimal strength and radiopacity with good biocompatibility. Unfortunately, the choices of appropriate biocompatible metals available as thin wall tubing for stent construction are somewhat limited. To achieve optimal radiopacity, the stent design of the present invention is adjusted to the specific radiopacity and strength characteristics of the metal from which the stent is fabricated. What is more, coatings such as parylene may be needed to avoid corrosion from stents with less biocompatible materials and/or dissimilar metals on the stent's exterior surface. Of extreme importance to the present invention is the achievement of optimal radiopacity in a stent that is only 0.004 inches wall thickness or less. Such a stent would have a pre-deployment outer diameter (profile) that would be at least 0.003 inches less than the open cell Tristar stent (Guidant Corp.) that has a wall thickness of 0.0055 inches. Ideally, the stent described herein would have a wall thickness between 0.0025 inches and 0.004 inches.

Described below are the novel design elements for open cell stents formed from stainless steel or a highly radiopaque metal such as tantalum, or plated with highly radiopaque materials like gold.

1. Tapered Strut Width for Stents Formed From Highly Radiopaque Metals

Although reducing the width of the diagonal section alone will reduce radiopacity without significantly affecting radial strength, by having a taper on the curved sections of the circumferential sets of strut members, a greatly reduced level of strain upon stent expansion can be achieved without sacrificing radial strength. This is extremely important as it allows a stent to be made much stronger than a stent with uniform width of the strut members while staying within the same strain limit for the material.

Tantalum is a metal that is used for stents and it is highly radiopaque. The optimal radiopacity for a stent design using tantalum could have uniform width for the circumferential sets of strut members and a wall thickness of 0.0025 inches. To provide more radial strength and to reduce the probability of the stent ends flaring out during deployment, a wall thickness of 0.003 inches to 0.035 inches would be highly desirable. With uniform width sets of strut members, a 0.035 inches wall thickness tantalum stent would be too bright under cine angiography. To reduce the radiopacity of the design without significantly impacting the radial strength of the deployed stent, the present invention envisions curved sections and diagonal sections either or both of which could have a variable or tapered width. The curved sections should be tapered (wider at the center compared to the ends) to reduce strain as previously described. The diagonal sections can be thinner in the center than at the ends to reduce radiopacity for the interior sets of strut members while maintaining a higher degree of radiopacity for the end set of strut members. It is envisioned that the novel open cell stent described herein might have wider diagonal sections for the end sets of strut members as compared to the interior sets of strut members. This feature would enhance the radiopacity of the end sets of strut members while retaining a moderate level of radiopacity for the interior sets of strut members. It is also envisioned to have both reduced width diagonals and/or reduced wall thickness for the interior sets of strut members. It is fluoroscopic visualization of the end sets of strut members that is most important for visualizing stents placed inside a coronary artery. Therefore, the end sets of strut members should have either or both a greater width of diagonal sections or a greater strut thickness as compared to those parameters of the interior sets of strut members.

2. End Sets of Strut Members with Thinner Curved Sections

Stent deliverability into curved coronary arteries is improved when the diagonal sections of the end sets of strut members have a decreased length as compared to the length of the diagonal sections of the interior sets of strut members. A shorter length of the diagonal sections will also reduce outward flaring upon expansion of the stent. Decreasing end flaring of the deployed stent is of particular importance for stents having very thin walls. Burpee and Fischell in U.S. Pat. No. 5,913,895 describe a stent with shorter diagonal sections in the end sets of strut members. The design of Burpee and Fischell is limited by the strain limit allowed for the end sets of strut members. As a result, if the end sets of strut members are made as strong as possible while being limited by the maximum allowable strain for that metal, the interior sets of strut members will not have optimized radial strength. The present invention envisions optimizing the radial strength for all circumferential sets of strut members for an open cell stent; i.e., the metal in all sets of strut members reaches the same, maximum allowable strain at the limiting diameter for the stent's expansion. To achieve this desired attribute, the stent described herein has curved sections of the end sets of strut members that are less wide than the curved sections of the interior sets of strut members.

3. Good Sidebranch Access While Maintaining Small Cell Size

The stents described herein are open cell stents having every other curved section of every interior set of strut members connected to an adjacent set of strut members by an undulating longitudinally extending link. Open cell stents connected with such an undulating connecting link should have the interior length of the perimeter of each of the stent's cells to be at least 9 mm in length. This design parameter allows each cell of the stent to be expanded to a circular diameter of approximately 3 mm (i.e., $9/\pi \cong 3$). This feature allows the "unjailing" of side branches of the artery into which the stent is placed. A cell for good side branch access should have an interior perimeter length between 9 mm and 15 mm. (i.e., an expandable circular diameter between 2.86 and 4.8 mm).

4. Flexible Undulating Longitudinal Links With Good Support Between Adjacent Sets of Strut Members To provide a strong bridge connection between adjacent circumferential sets of strut members, the flexible undulating longitudinal connecting links should have nearly equal extent in the circumferential direction on each side of a line drawn between the attachment points of the flexible undulating longitudinal connecting link to the curved sections of adjacent sets of strut members. "S", "N" and inverted "N" shapes for the connecting links inherently have equal circumferential displacement on each side of the line connecting their attachment points. It is envisioned that "M" or "W" shaped or other types of connecting links can be used if there is an equal circumferential extent of these undulating links on each side of a line that joins the attachment points of these links to the sets of strut members.

5. Variable Thickness Radiopaque Coatings

The NIROYAL stent has a uniform thickness of gold plating, which makes the center too radiopaque as compared to the radiopacity of the end sets of strut members. The Fischell et al invention described in U.S. Pat. No. 6,086,604 teaches stents having gold placed only on the end sets of strut members. This creates a potential for corrosion from dissimilar metals, namely, gold and stainless steel. The present invention envisions a gold coating that is sufficiently thick on the end sets of strut members to provide optimal radiopacity with a thin coating of gold on the rest of the stent. This design prevents obscuring of the arterial lumen while providing an exterior surface for the stent that is a single metal thus avoiding electrolytic corrosion.

6. Polymer Coatings for Stents Coated With Gold or Having Dissimilar Metal Surfaces For stents with non-biocompatible or dissimilar metals, the present invention envisions the use of a polymer such as parylene to coat the entire outer surface of the stent. This would improve biocompatibility and also allow attachment of organic compounds such as heparin or phosphorylcholine for reduced thrombogenicity or drugs such as Taxol or Rapamycin for reduced cell proliferation and a decreased rate of restenosis. It is also known that highly radiopaque materials like tungsten can be mixed into polymers. A stent coating including a plastic with mixed in radiopaque metal could be used to enhance both radiopacity and biocompatibility. Such a polymer coating could also be advantageous with a gold-coated stent.

7. Attachment of a Drug Coating

It is also envisioned that any one of the following drugs could be attached to the stent to decrease restenosis and/or subacute thrombosis: Rapamycin, Alkeran, Cytoxan, Leukeran, Cis-platinum, BiCNU, Adriamycin, Doxorubicin, Cerubidine, Idamycin, Mithracin, Mutamycin, Fluorouracil, Methotrexate, Thoguanine, Toxotere, Taxol, Etoposide, Vincristine, Irinotecan, Hycamptin, Matulane, Vumon, Hexalin, Hydroxyurea, Gemzar, Oncovin and Etophophos.

8. Providing a Variable Wall Thickness

The present invention also envisions next generation manufacturing techniques using photoetching whereby a stent pattern is etched into a thin-walled metal tube. These techniques already can produce variations in wall thickness as well as strut width for any stent pattern. The present invention envisions use of these techniques to create stents with optimal radiopacity. In particular for a stent formed from a single metal or alloy, thicker metal (i.e., greater wall thickness) at each end of the stent could increase radiopacity there as compared to the interior section of the stent.

It is also envisioned that any of the above optimal radiopacity stent designs may be used with plastic coatings such as parylene, antithrombogenic coatings such as heparin or phosphorylcholine or anti-proliferative coatings such as Taxol or Rapamycin, or any other drug as listed above.

Thus an object of the present invention is to have increased longitudinal flexibility for the stent by having some curved sections of each circumferential set of strut members being unconnected to the curved sections of the adjacent circumferential set of strut members with the other curved sections being connected by highly flexible, undulating longitudinal connecting links.

Another object of the present invention is to prevent flaring of the unconnected strut members by having a shorter longitudinal length for the unconnected strut members.

Still another object of the invention is to have generally shorter longitudinal lengths for all the strut members in the circumferential sets of strut members at the stent ends to reduce the tendency for end flaring of the stent.

Still another object of the invention is to decrease the propensity of the stent to have end flaring by having each curved section of the end set of strut members either being unconnected to the curved section of the adjacent (interior) set of strut members or being connected by a highly flexible undulating longitudinal connecting link.

Still another object of the invention is to connect the flexible longitudinal connecting links to the curved sections of the sets of strut members at a point that is close to the line where the diagonal sections join the curved sections, thus further reducing the propensity for end flaring.

Still another object of the invention is to have flexible longitudinal connecting links that are adapted to readily increase their longitudinal length when the balloon is inflated; thus minimizing the extent of stent foreshortening upon stent deployment.

Still another object of the present invention to have a stent that has sets of circumferential strut members with tapered curved sections, the center of the curved sections being wider than the ends of the curved sections so as to reduce plastic strain as the stent is expanded as compared to a curved section with uniform width.

Still another object of the present invention is to have a stent with tapered diagonal sections in the sets of strut members where the center of the diagonal section is narrower than the ends of the diagonal section to reduce the radiopacity of interior sets of strut members of the stent as compared to a stent with diagonal sections having a uniform width.

Still another object of the invention is to have a stent with decreased wall thickness of the interior set of strut members as compared to the end set of strut members so as to have a comparatively higher radiopacity for the end sets of strut members.

Still another object of the present invention is to have a stent having end sets of strut members with tapered diagonal sections that are wider at their center compared to their ends to increase the radiopacity of the end sets of strut members.

Still another object of the present invention is to have end sets of strut members having both shorter diagonal sections and thinner width curved sections as compared to those sections in the interior sets of strut members.

Still another object of the present invention is to have a tantalum stent with wall thickness less than 0.035 inches having tapered sets of strut members whereby the diagonal sections of the interior sets of strut members are less wide than the width at the center of the curved sections.

Still another object of the present invention is to have an open cell stent design with maximum post-deployment interior cell perimeter length that is equal to or greater than 9 mm.

Still another object of the present invention is to have a stent with a radiopaque metal coating where the radiopaque metal coating has greater wall thickness on the end sets of strut members as compared to thickness of the radiopaque metal coating on the interior sets of strut members.

Still another object of the present invention is to have an open cell stent design with "S" or "N" or inverted "N" or other shaped flexible undulating longitudinal connecting links wherein the circumferential extent of each flexible undulating longitudinal connecting link is approximately equal on each side of a line drawn between the proximal and distal attachment points of the flexible undulating longitudinal connecting link.

Still another object of the present invention is to have the stent with optimized radiopacity formed with an outer surface that is plastic coated to improve biocompatibility.

Still another object of the present invention is to have the stent with optimized radiopacity that is coated with a plastic material and an additional material to prevent thrombus formation and/or restenosis; the additional material being selected from the group that includes Rapamycin, Alkeran, Cytoxan, Leukeran, Cis-platinum, BiCNU, Adriamycin, Doxorubicin, Cerubidine, Idamycin, Mithracin, Mutamycin, Fluorouracil, Methotrexate, Thoguanine, Toxotere, Taxol, Etoposide, Vincristine, Irinotecan, Hycamptin, Matulane, Vumon, Hexalin, Hydroxyurea, Gemzar, Oncovin and Etophophos.

Still another object of the present invention is to have a stent coated with a plastic material that includes a radiopaque filler material.

These and other objects and advantages of this invention will become obvious to a person of ordinary skill in this art upon reading the detailed description of this invention including the associated drawings as presented herein.

DETAILED DESCRIPTION OF THE INVENTION

Although stents are in fact thin-walled, lace-like, cylindrical tubes, they are best illustrated in the form of a flat, two-dimensional layout view as shown in FIGS. 1–7 inclusive.

Figure 1:
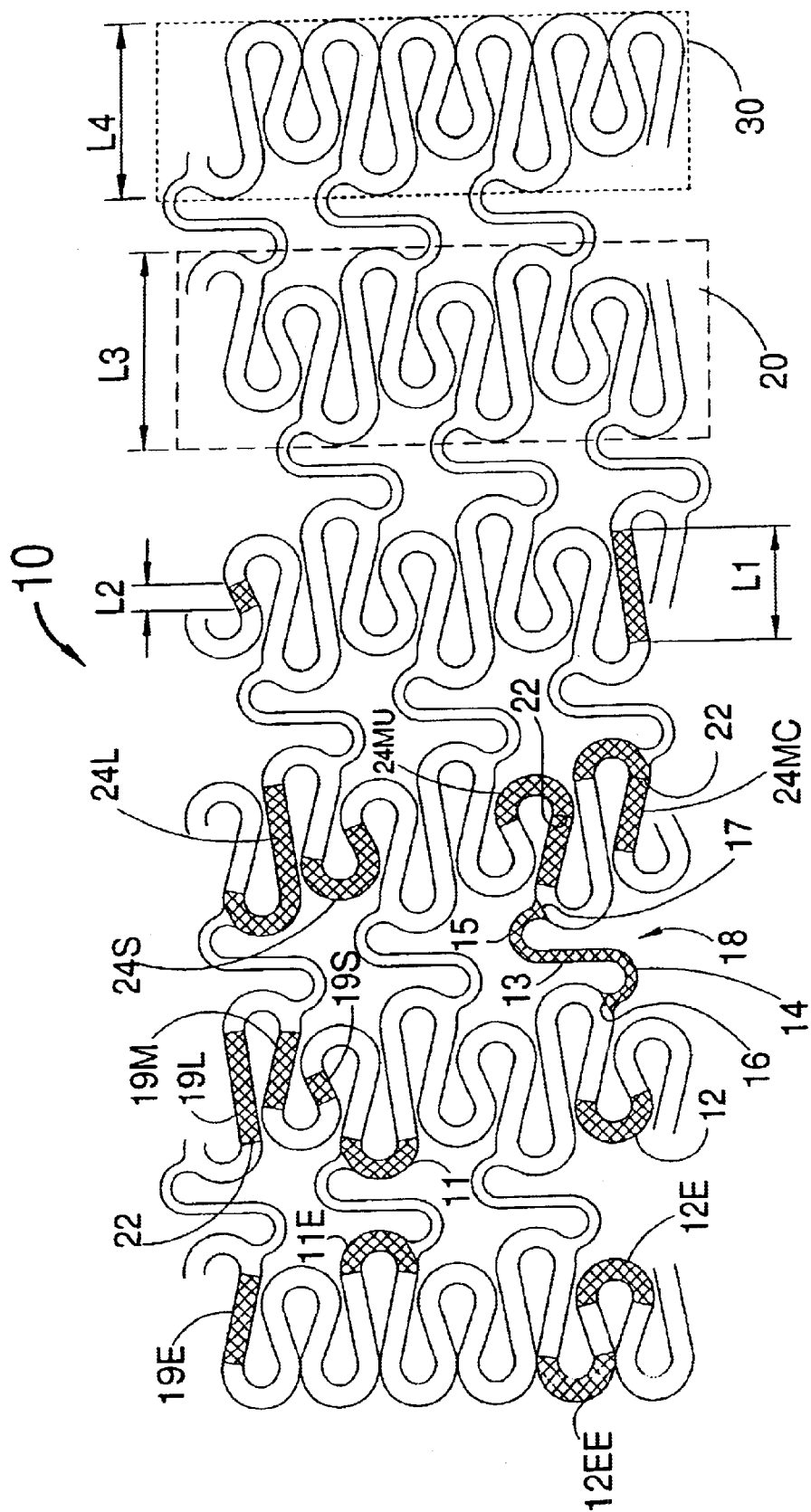
FIG. 1 is a layout view of the stent of the present invention in its pre-deployed state as it would be crimped onto the balloon of a balloon expandable stent delivery system.

FIG. 1 is a flat, layout view of a cylindrical stent 10 wherein each of the stent's top ends would be joined to each of the stent's bottom ends to form the cylindrical stent 10 in its pre-deployed, lace-like, cylindrical form.

The pre-deployed stent 10 of the present invention is shown in FIG. 1 as having a multiplicity of interior circumferential sets of strut members 20 and two end circumferential sets of strut members 30, each indicated within a dashed rectangle. For the stent 10, the connected curved sections 11 and 11E and the unconnected curved sections 12 and 12E are shown in crosshatch in FIG. 1. Also shown in crosshatch in FIG. 1 is the long diagonal section 19L, medium length diagonal section 19M and short diagonal section 19S. Each of the interior sets of strut members 20 consists of at least one long connected strut member 24L, at least one medium length connected strut member 24MC, at least one medium length unconnected strut member 24MU and at least one unconnected strut member 24S. Each of the long connected strut members 24L consists of a long diagonal section 19L joined along the line 22 to a connected curved section 11. Each medium strut member 24MC or 24MU consists of one medium diagonal section 19M connected along a line 22 to a curved section 11. Each short unconnected strut member 24S consists of a short diagonal section 19S joined to an unconnected curved section 12. As shown in FIG. 1, the longitudinal length of the long diagonal section 19L is L1 and the longitudinal length of the short diagonal section is L2. As clearly seen in FIG. 1, the longitudinal length L1 is longer than the longitudinal length L2, i.e., L1>L2. For an effective stent design, L1 should be at least 0.1 mm longer than L2.

Each of the connected curved sections 11 is joined to an adjacent curved section 11 or 11E in the adjacent set of strut members by means of a longitudinally extending, flexible longitudinal connecting link 18 that consists of a interior segment 13, a bottom curved segment 14 and a top curved segment 15. The bottom curved segment 14 is fixedly joined to a connected curved section 11 along the junction line 16. The top curved segment is joined to a connected curved section 11 along the junction line 17. The optimal placement of the junction lines 16 and 17 is at or near the connecting line 22 that joins a curved section 11 (or 11E) to a diagonal section 19L, 19M or 19E. Although an "S" type flexible strut 18 is shown in FIG. 1, it should be understood that any flexible longitudinal connecting link shape that can readily lengthen or shorten in its longitudinal extent as the pre-deployed stent is advanced through a curved vessel could be used. Such flexible links are, for example, described in U.S. patent application Ser. No. 09/192,101. Thus it is anticipated that the flexible link 18 could be in the form of an "N", an inverted "N", an "M" or a "W" or any other shape (such as a "U") that can easily change its length in the longitudinal direction as the pre-deployed stent is advanced through or placed into a curved artery.

As previously stated, the unconnected diagonal sections 19S and 19M have a decreased longitudinal extent as compared to the longitudinal extent of the connected diagonal sections 19L. This design provides an open area so that the bottom curved segments 14 of the flexible longitudinal connecting links 18 do not interfere with the top curved segments 15 when the stent 10 is crimped onto a balloon of a stent delivery system. Thus a decreased profile (i.e.; smaller outer diameter) can be achieved for the pre-deployed stent 10 without causing the bottom curved segment 14 to be placed over (or beneath) the top curved segment 15.

Connected curved sections 11 do not have a tendency to flare outward when the pre-deployed stent 10 is advanced through a curved vessel because the longitudinal connecting struts 18 exert an inward radial force that tends to prevent such flaring. Therefore, one can have connected strut members 24L that are comparatively long and still they will not flare out to engage the vessel wall when the stent 10 is advanced through a curved vessel. However, without longitudinal connecting links, an unconnected curved section (such as the unconnected curved section 12) will tend to flare outward as the stent 10 is advanced around a bend in a curved vessel. To minimize such tendency to flare, the unconnected strut members 24S have a short diagonal section 19S with a reduced longitudinal length L2 as compared to the longitudinal length L1 of the diagonal section 19L of the connected strut members 24L. The unconnected medium strut member 24MU has a diagonal section 19M that has a reduced length as compared to the diagonal 19L of the long strut member 24L. A reduced length is defined herein as being at least 0.1 mm shorter than the length L1 of the long diagonal 19L. By this design, the pre-deployed stent 10 will have little or no flaring or fish-scaling for all interior curved sections of the stent 10. However, there will always be some tendency to have end flaring for each of the end curved sections 12EE of the end set of strut members 30. Reduced flaring of the end curved sections 12EE is accomplished by having comparatively short diagonal sections 19E and also by the location of the attachment line 22 where the links 18 are joined to the curved sections 11E of the end set of strut members 30. The advantageous design of the stent 10 of FIG. 1 in reducing the propensity for end flaring is best explained by first referring to FIGS. 2 and 3 that illustrate prior art stent designs that tend to have a significant propensity for end flaring.

Figure 2:
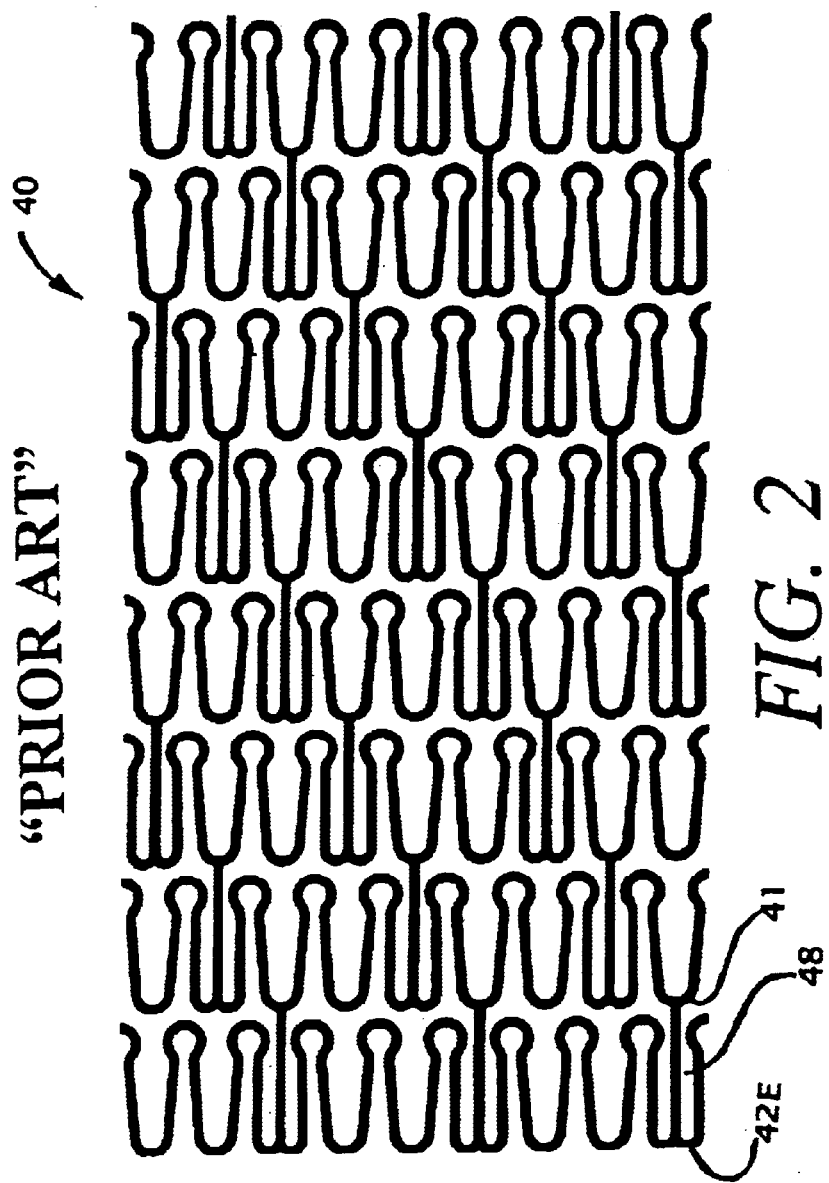
FIG. 2 is a layout view of a prior art stent showing a straight longitudinal connecting link joining the inside of a curved section of a circumferential set of strut members to the outside curved section of the adjacent circumferential set of strut members.

FIG. 2 illustrates a prior art stent design which is the Multi-Link RX Ultra marketed by Guidant Corporation. In this design, the stent 40 has an end curved section 42E that has an inside connection of a straight longitudinal connecting link 48 that connects to the outside of the interior connecting curved section 41. Because the connecting strut 48 is formed out of the wall of a straight tube, it is straight, comparatively long and it tends to remain straight as the stent 40 mounted on a balloon is advanced through a curved vessel. Thus the longitudinal connecting link 48 can actually force the end curved section 42E to flare outward in a highly curved vessel.

Figure 3:
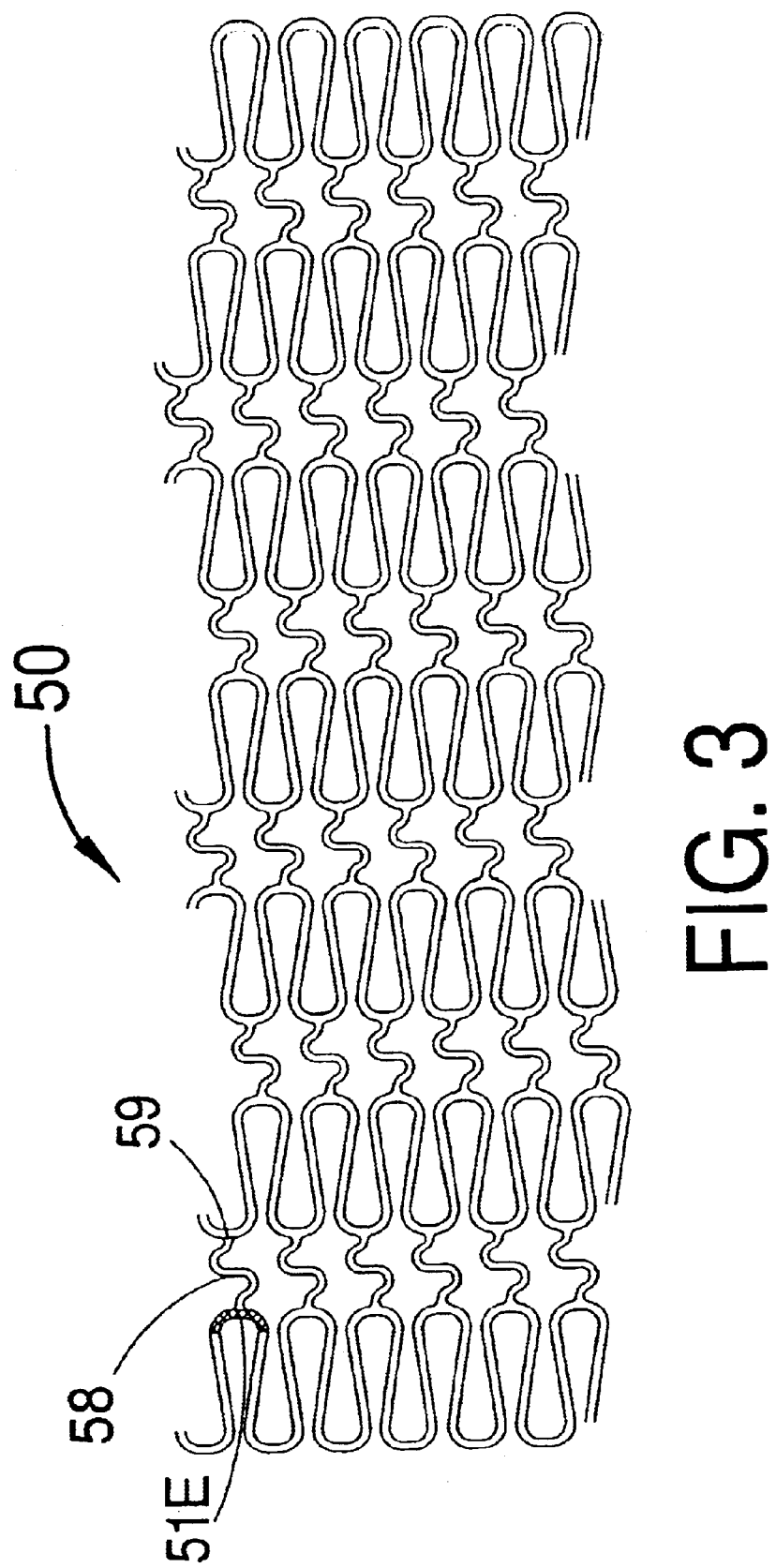
FIG. 3 is a layout view of a closed cell stent having flexible longitudinal connecting links attached at the center of the outside of all the curved sections of every circumferential set of strut members.

FIG. 3 illustrates a stent design that has an "S"-shaped connecting link 58 connected at the centered, longitudinal end point 59 to an end connected curved section 51E. Thus there is some tendency for the short, straight section of the link 58 where it joins the curved section 51E to cause the end struts of the stent 50 to flare outward. It should be understood however, that the design of FIG. 3 has a much decreased tendency for end flaring as compared to the design of FIG. 2.

Returning now to a discussion of FIG. 1, because the connection lines 16 and 17 are not at the centered, longitudinal end point of the connecting curved end section 11E, the flexible longitudinal connecting links 18 cannot exert a substantial force onto the interior end curved sections 11E to cause end flaring. In fact, because of the shape of curved sections 14 and 15, and because of their off-center attachment to the connected curved end section 11E, the longitudinal connecting strut 18 can only exert an insignificant torque onto the curved end sections 11E. Thus, the connecting struts 18 do not cause any significant tendency to have any of the strut members of the end set of strut members 30 flare outward in curved vessels. Put another way, the undulating longitudinal connecting link 18 will tend to follow the curve within a curved vessel and will not have a tendency to remain straight in the longitudinal direction as is the case for the straight longitudinal connecting strut 48 shown in FIG. 2. Thus the flexible longitudinal connecting link 18 has a dramatically reduced propensity to cause end flaring of the stent 10.

Another factor in decreasing end flaring (as seen in FIG. 1) is that the longitudinal length L3 of the interior sets of strut members 20 is greater by at least 0.05 mm as compared to the longitudinal length L4 of the end sets of strut members 30. Also, the attachment point for the flexible longitudinal connecting links 18 along the line 16 or 17 is such that the effective longitudinal length that can cause end flaring is even less than the length L4. For a connecting link such as the connecting strut 58 of FIG. 3 that is connected at the center of an end curved section, there would be an increased tendency for end flaring as compared to the design of FIG. 1.

Figure 4:
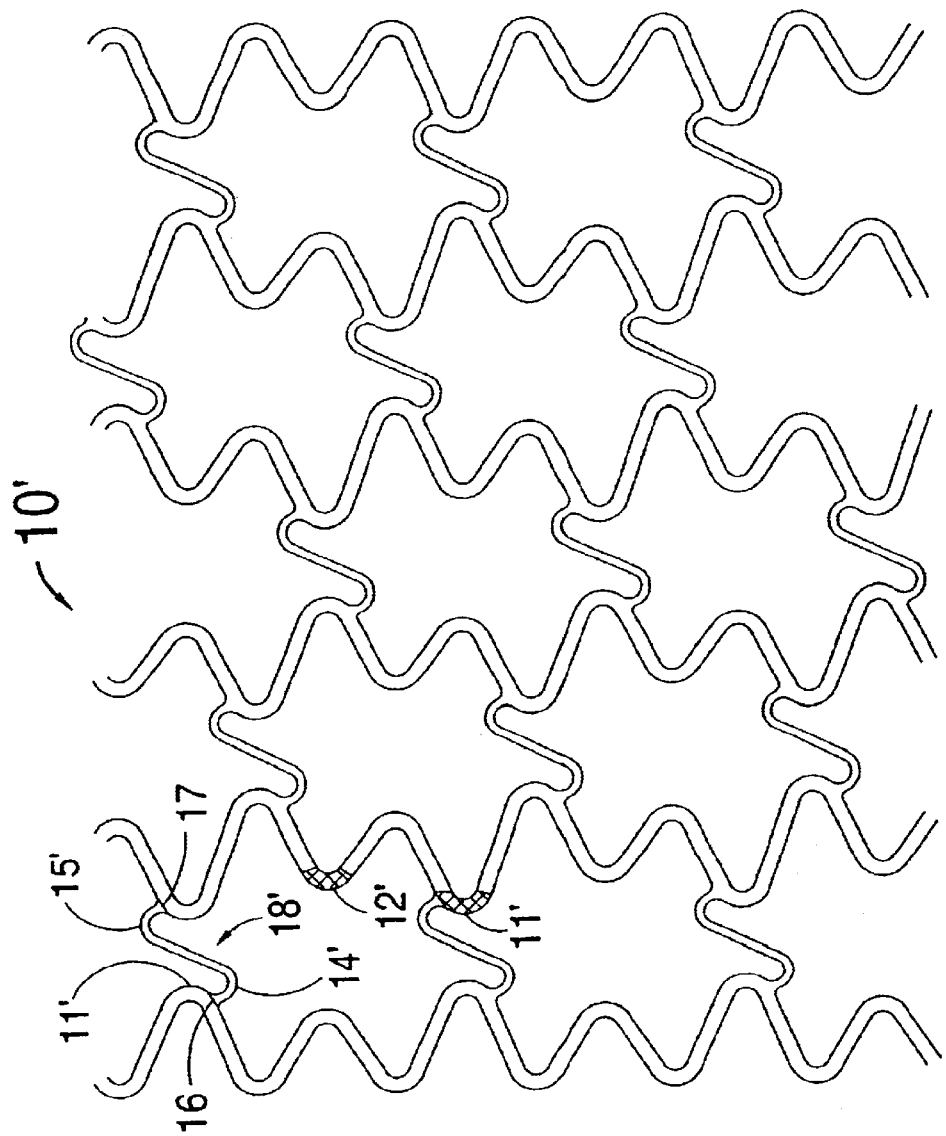
FIG. 4 is a layout view of the stent of FIG. 1 shown in its deployed state.

FIG. 4 is a flat, layout view of the deployed stent 10' showing the deployed curved sections 11' and 12' and the shape of the deployed flexible longitudinal connecting link 18'. Because the longitudinal length decreases for all circumferential sets of strut members 20 or 30 when the balloon on which the stent 10 is mounted is inflated, there is a tendency for the stent 10' to foreshorten in its longitudinal length as compared to the longitudinal length of the pre-deployed stent 10. However, because the strut members 20 and 30 are firmly crimped onto the balloon, as the balloon is inflated, they have a longitudinal retention force from friction with the balloon surface that is great enough to cause the comparatively weak longitudinal connecting links 18' to lengthen in the longitudinal direction. Therefore, as the balloon is expanded, the longitudinal connecting links 18' will actually be stretched in the longitudinal direction, thus increasing their longitudinal length during balloon inflation. The effect of lengthening the longitudinal extent of the longitudinal connecting links 18' is to decrease the foreshortening of the deployed stent 10'.

Figure 5:
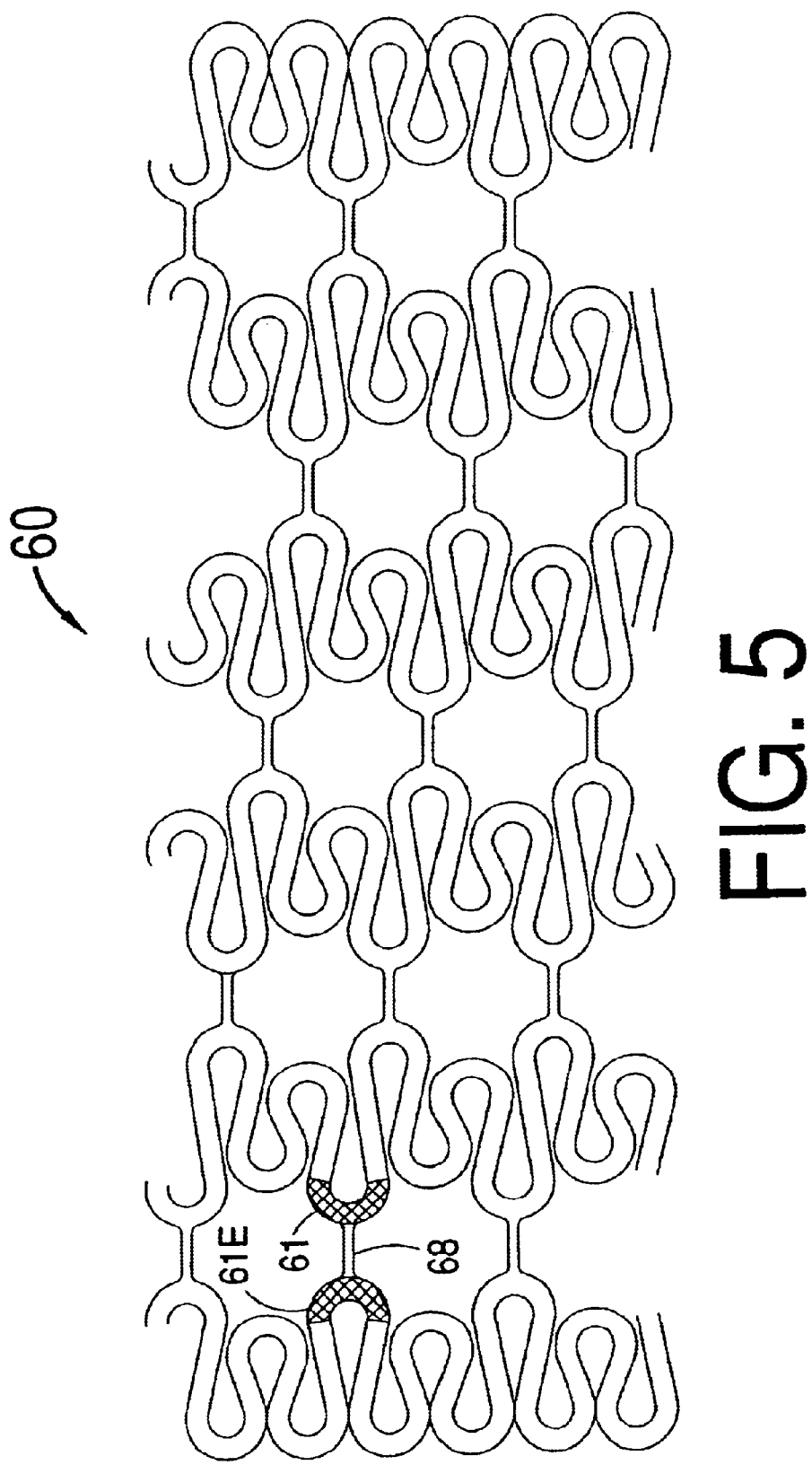
FIG. 5 is a layout view of a stent of the present invention in which alternate adjacent curved sections are connected by straight longitudinal connecting links.

Although the greatest longitudinal flexibility for the stent 10 is obtained by connecting some of adjacent sets of strut members with flexible longitudinal connecting links (like the link 18), it should be understood that short, straight links could be used to connect adjacent curved sections such as 12 and 12E. This design concept is shown in FIG. 5 that is a layout view of a stent 60 that has connected curved sections 61 and 61E that are connected by straight connecting links 68. Of course it should be understood that any combination of straight and flexible longitudinal connecting links could be used. Furthermore, for any one stent, a different number and/or different type of connecting links could join different sets of adjacent strut members. The number of connecting links connecting any pair of adjacent sets of strut members could be as few as one or as many as eight. The design of FIG. 5 has several advantages over the design of FIG. 2 although both use straight longitudinal connecting links to connect the circumferential sets of strut members. The stent of FIG. 5 only connects to the outsides of the curved sections 61 or 61E. For the same width of the circumferential sets of strut members this will reduce the minimum crimpable diameter of the stent 60 as compared to the stent 40 of FIG. 2 because the straight longitudinal connecting links 48 of the stent 48 separate the curved sections of some of the strut members when the stent 40 is crimped down onto a balloon.

Figure 6:
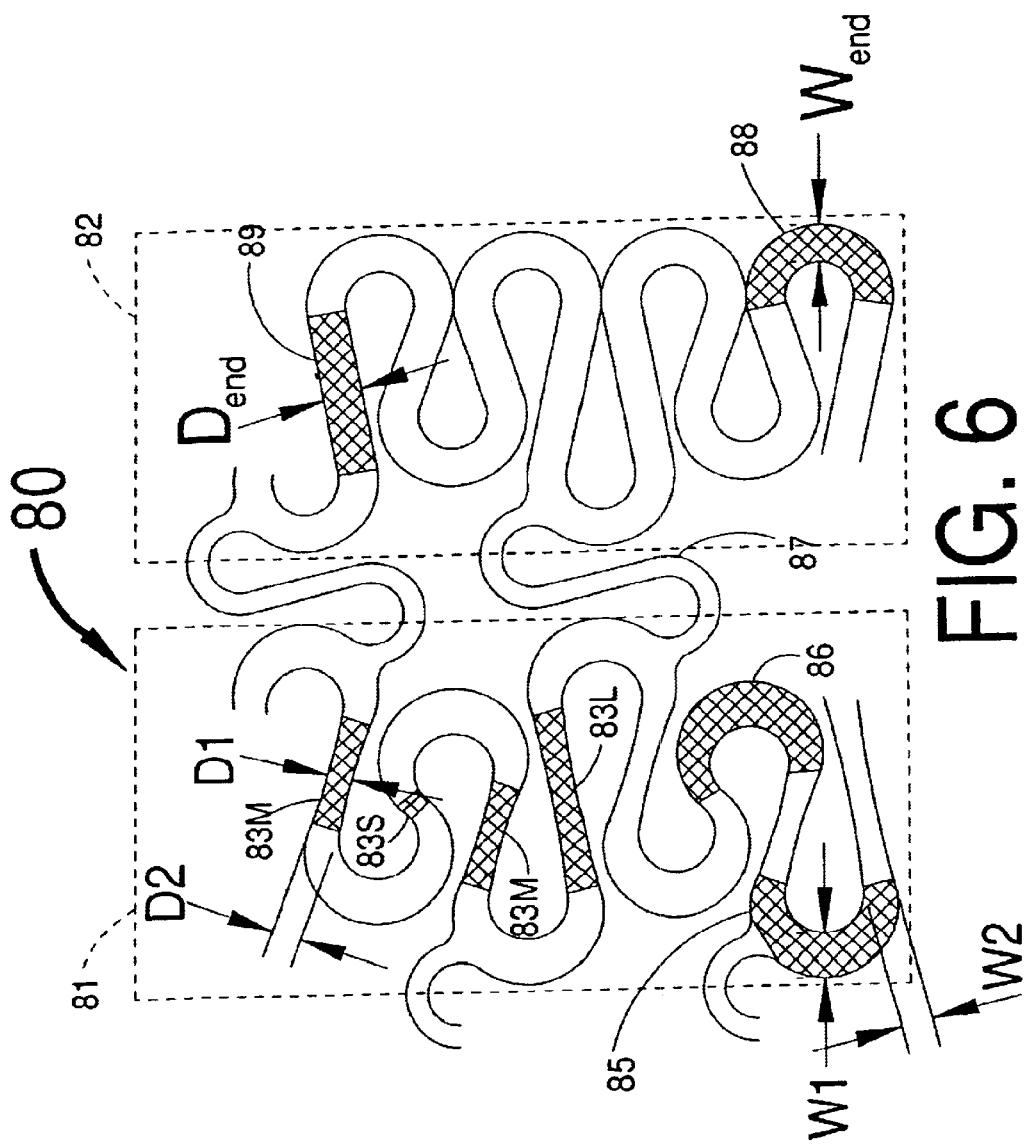
FIG. 6 is a layout view of a stent of the present invention showing curved sections and diagonal sections for the interior circumferential sets of strut members each of which has a tapered width.

FIG. 6 illustrates an alternative embodiment of the present invention that is an open cell stent 80 having an interior circumferential set of strut members 81 and an end circumferential set of strut members 82. Of course, every open cell stent 80 would have one end set of strut members 82 at each end of the stent and at least one interior set of strut members 81 situated between the end sets of strut members 82. The interior set of strut members 81 includes long diagonal sections 83L, medium length diagonal sections 83M, short diagonal sections 83S, connected curved sections 85 and unconnected curved sections 86. The width W1 at the center of each of the curved sections 85 is greater than the width W2 at each end of the curved sections 85. This design of a tapered strut width for the curved sections 85 allows greater radial strength for the circumferential sets of strut members 81 for the same level of strain when the stent 80 is expanded.

For the stent 80, at least the medium length diagonal sections 83M and the long diagonal sections 83L are tapered to have a reduced width D1 at their centers and an increased width D2 at their ends where D2=W2. This narrowing at the center of the diagonal sections reduces the radiopacity of the interior region of the stent 80.

The width of all the curved and diagonal sections of the end circumferential sets of strut members 82 is shown in FIG. 6 to be uniform; i.e., Wend=Dend. Thus the curved sections 88 and diagonal sections 89 of the end set of strut members have the same width. An optimum design has Wend thinner than W1. The relative magnitude of W1 and Wend can be adjusted so that the stent 80 when fully deployed will have the same maximum strain for each of the circumferential sets of strut members 81 or 82 even though the end set of strut members 82 have shorter diagonals as compared to the length of the longest diagonal sections 83L of the interior set of strut members 81. This is a very important design parameter for the stent so as to optimize the stent's radial strength within the specific limits on allowed strain at the full deployment diameter of the stent.

Figure 7:
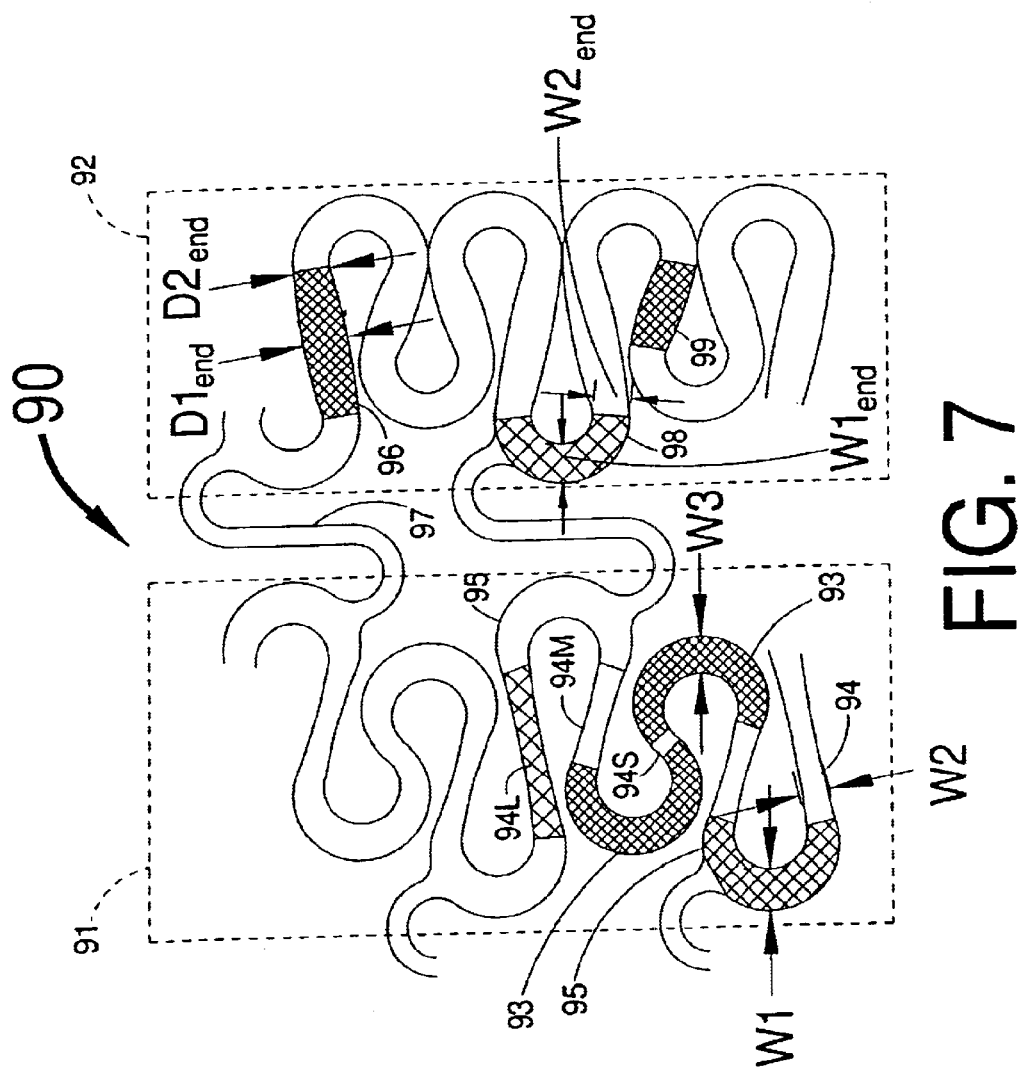
FIG. 7 is a layout view of a stent of the present invention showing curved sections and diagonal sections for the interior and end circumferential sets of strut members each of which has a tapered width for each diagonal section.

FIG. 7 is another embodiment of the present invention that differs from the design of FIG. 6 in that the end set of strut members 92 of the stent 90 have a variable width for both the curved sections 98 and the diagonal sections 96. The stent 90 has interior circumferential sets of strut members 91 and end circumferential sets of strut members 92. For the interior sets of strut members 91, the connected curved sections 95 have a center width W1 and a decreased end width W2 wherein W1 is at least 0.001 inches greater than W2. The unconnected curved sections 93 will have the same width at their ends of W2, but their width at the center of the unconnected curved sections will be W3 where W3 is less than W1 but wider than W2. As is the case for FIG. 6, the diagonal sections 94L and 94M of the interior sets of strut members 91 are tapered to have a thinner width at the center of each diagonal 94L or 94M as compared to the width at the end of each diagonal section 94L or 94M. The shortest diagonal sections 94S would probably not be tapered. The widths W1 and W3 would be adjusted to equalize the strain at maximum stent deployment diameter for each curved section 93 or 95 of each of the interior sets of strut members 91. Furthermore, the curved sections 98 of the end set of strut members 92 can have an increased width at the center, W1end compared to the width W2end at each end of the curved sections 98, but W1 would be wider than W2end. Again it should be pointed out that these width variations are used to equalize the strain for all the stent's circumferential sets of strut members when the stent 90 is deployed to the maximum diameter for which it is designed.

It can be clearly seen in FIG. 7 that at least the longest diagonal section 96 of the end set of strut members 92 is tapered in an opposite sense as compared to the tapers of the diagonal sections 94L and 94M of the interior set of strut members. The purpose for this is to enhance the radiopacity of the end set of strut members 92 while diminishing the radiopacity of the interior set of strut members 91. To accomplish this, D1end is wider than D2end. This condition optimizes the radiopacity of the stent so as to satisfy the needs of the interventional cardiologist or radiologist who has to clearly see the ends of the stent 90 but requires less visibility for the interior region of the stent 90. It should be noted that this variation in radiopacity is accomplished with a single metal such as tantalum without the need for gold plating or gold discs inserted into a stainless steel stent. Anytime a second metal is used, the possibility of electrolytic corrosion can exist and/or there can be an enhanced rate of restenosis or subacute thrombosis. Optimally, the metal would have a high density, for example tantalum. An optimum wall thickness for such a stent would be between 0.002 and 0.004 inches.

For both the stents 80 and 90, it should be noted that the longitudinal lengths of the interior circumferential sets of strut members 81 and 91 are longer than the longitudinal lengths of the end circumferential sets of strut members 82 and 92. This condition provides for greater radial rigidity for the end set of strut members 82 and 92 and decreases the propensity of the stent 80 or 90 to have outward flaring (fish-scaling) of the end strut members. This is highly desirable to avoid the stent engaging the arterial wall as it is advanced through curved blood vessels.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A half open, half closed hybrid cell stent in the form of a thin-walled, multi-cellular, tubular structure having a multiplicity of circumferential sets of strut members, each set of strut members being longitudinally separated each from the other, each set of strut members being connected to adjacent sets of strut members by longitudinal connecting links having at least one curved strut therein and each set of strut members forming a closed, ring-like cylindrical portion of the stent, each set of strut members consisting of a multiplicity of connected curved sections and diagonal sections, each curved section having two ends and a center situated there between, at least one set of strut members having at least half of the curved sections within the set of strut members having a tapered shape wherein the width at the center of a curved section with a tapered shape is greater than the width at the ends of a curved section with tapered shape, and no greater than half of the curved sections of each set of strut members connected to the longitudinal connecting links, and wherein said longitudinal connecting links comprise further comprising a multiplicity of sets of flexible links with each set of flexible links connecting two of the multiplicity of sets of strut members, each set of flexible links consisting of a multiplicity of individual flexible links, each individual flexible link being a single undulating structure that extends generally in the longitudinal direction that is parallel to the stent's longitudinal axis and each individual flexible link having two ends, each one of the two ends being fixedly attached to one curved section of the multiplicity of sets of strut elements at an attachment point situated between the center and the end of that curved section.

2. The stent of claim 1 wherein the curved sections of one or more of the sets of strut members have inside and outside surfaces in the shape of circular arcs, each circular arc having a center with the centers of the two arcs being longitudinally displaced one from the other.

3. The stent of claim 1 wherein the width at the center of the curved sections with a tapered shape is at least 0.001 inches greater than the width at the ends of the curved section with tapered shape.

4. The stent of claim 1 wherein all curved sections have a tapered shape.

5. The stent of claim 1 wherein the sets of strut members include end sets of strut members located at each end of the stent and interior sets of strut members positioned between the end sets of strut members, the end sets of strut members having an average length of its diagonal sections that is shorter than the average length of the diagonal sections of the interior sets of strut members.

6. The stent of claim 5 wherein all curved sections of every interior set of strut members have a tapered shape.

7. The stent of claim 5 wherein the curved sections of the end sets of strut members each have a respective strut width, and the strut width at the center of the curved sections of the end sets of strut members is less than the strut width at the center of the curved sections of the interior sets of strut members.

8. The stent of claim 5 wherein the diagonal sections of the interior sets of strut members have a center and two ends, at least one of the diagonal sections of the interior sets of strut members has a tapered shape wherein the width of the at least one diagonal section is different at the center of the diagonal section as compared to the width at either end of that diagonal section.

9. The stent of claim 8 wherein the width of the at least one diagonal section of the interior sets of strut members is less at the center of that diagonal section compared to the width at either end of that diagonal section.

10. The stent of claim 8 wherein the width of the at least one diagonal section of the interior sets of strut members is greater at the center of that diagonal section as compared to the width at either end of that diagonal section.

11. The stent of claim 8 wherein all the diagonal sections of all of the interior sets of strut members have a tapered shape.

12. The stent of claim 5 wherein all of the diagonal sections of the end sets of strut members have a tapered shape.

13. The stent of claim 12 wherein the tapered diagonal sections of the ends of strut members having a tapered shape have a greater width at their center compared to their ends to enhance the radiopacity of the end set of strut members.

14. The stent of claim 1 wherein the stent is coated with a plastic material.

15. The stent of claim 14 wherein the plastic material is parylene.

16. The stent of claim 14 where a drug is attached to the plastic material, the drug being selected from the group that includes Rapamycin, Alkeran, Cytoxan, Leukeran, Cisplatinum, BiCNU, Adriamycin, Doxorubicin, Cerubidine, Idamycin, Mithracin, Mutamycin, Fluorouracil, Methotrexate, Thoguanine, Toxotere, Taxol, Etoposide, Vincristine, Irinotecan, Hycamptin, Matulane, Vumon, Hexalin, Hydroxyurea, Gemzar, Oncoivin and Etophophos.

17. The stent of claim 14 wherein the drug is heparin.

18. The stent of claim 14 wherein the plastic material has a highly radiopaque material mixed into the plastic material to form a radiopacity coating.

19. The stent of claim 17 wherein the radiopaque material is powdered tungsten.

20. The stent of claim 17 wherein the thickness of the coating is greater on the end set of strut members compared to the thickness of the coating at the longitudinal center of the stent.

* * * * *